United States Patent [19]
Nijsten et al.

[11] Patent Number: 5,779,945
[45] Date of Patent: Jul. 14, 1998

[54] PROCESS FOR PRODUCING GRANULES

[75] Inventors: Pieter J. B. Nijsten, Meerssen; Peter J. M. Starmans, Nuth, both of Netherlands

[73] Assignee: DSM N.V., Heerlen, Netherlands

[21] Appl. No.: 838,131

[22] Filed: Apr. 15, 1997

[30] Foreign Application Priority Data

Apr. 15, 1996 [NL] Netherlands ................. 1002862

[51] Int. Cl.$^6$ .................................................. B29B 9/08
[52] U.S. Cl. .................... 264/7; 23/313 R; 23/313 FB; 23/313 P; 264/37.29; 264/117
[58] Field of Search .................... 264/7, 37.29, 117; 23/313 R, 313 FB, 313 P

[56] References Cited

U.S. PATENT DOCUMENTS

| 3,398,191 | 8/1968 | Thompson et al. |
|---|---|---|
| 3,700,461 | 10/1972 | Dickens, Jr. ............ 23/313 FB |
| 3,705,794 | 12/1972 | Czurak et al. |
| 3,969,546 | 7/1976 | Saeman |
| 3,989,470 | 11/1976 | Czurak et al. |
| 4,118,524 | 10/1978 | Saeman |
| 4,219,589 | 8/1980 | Niks et al. |
| 4,501,773 | 2/1985 | Nioh et al. |
| 4,619,843 | 10/1986 | Mutsers |
| 4,954,134 | 9/1990 | Harrison et al. ............ 23/313 R |
| 5,552,099 | 9/1996 | Wunder et al. ............ 264/117 |

FOREIGN PATENT DOCUMENTS

| 0 026 918 a1 | 4/1981 | European Pat. Off. |
|---|---|---|
| 0 141 436 A2 | 5/1985 | European Pat. Off. |
| 7806213 | 6/1978 | Netherlands |

OTHER PUBLICATIONS

The British Sulphur Corporation Ltd., 'Nitrogen'—'Special Techniques Give Coarser, Stronger Products and Less Pollution'.

*Primary Examiner*—Mary Lynn Theisen
*Attorney, Agent, or Firm*—Pillsbury, Madison & Sutro LLP; Cushman, Darby & Cushman Intellectual Property Group

[57] ABSTRACT

A process for producing granules from a liquid composition which includes the steps of applying the liquid composition onto solid particles of the same composition circulating in the granulation zone of a granulator, thereby causing particles to grow, discharging a stream of grown particles from the granulation zone, cooling this stream in a cooler, and dividing the stream exiting the cooler, in a size-sorting apparatus, into three streams of grown particles based on size. The stream of desired-sized particles is withdrawn for future use or processing, the stream of undersized particles is returned to the granulation zone and the stream of oversized particles is sent to a size-reducing apparatus for crushing, with the resulting crushed particles recycled back to the cooler located downstream of the granulator and upstream of the size-sorting apparatus.

13 Claims, 1 Drawing Sheet

PROCESS FOR PRODUCING GRANULES

BACKGROUND OF THE INVENTION

1. Field of the Invention

The invention relates to a process for producing granules from a liquid material by applying the liquid material onto solid particles circulating in the granulation zone of a granulator, thereby causing particle growth. The stream of particles exiting from the granulation zone is then cooled in a cooler, and sorted by a size-sorting apparatus into three streams of particles based on size: desired, under, and over sized particles. The stream of undersized particles is returned to the granulation zone while the stream of desired size particles is sent to product storage. The stream of oversized particles is sent to a size-reducing or crushing apparatus where it is crushed and then sent back to the cooler. The stream of desired-sized particles is withdrawn for future use or sale.

2. Description of the Related Art

Various processes by which solid particles can be produced from liquid materials, such as solutions, melts or suspensions, are well known in the art. Of particular interest are the granulation processes, such as that described in Nioh et al. (EP-A-0-026-918). Nioh et al. describe a spouted-bed granulation process, in which a liquid material, in a gas stream, is passed centrally from under and upward through a mass of particles and a number of particles are entrained from this mass by the gas stream and which subsequently, when the velocity of the gas stream decreases, fall back onto the surface of the mass of particles. In this mass of particles there are also present particles originating from a stream of undersized particles and from a stream of oversized particles after being crushed in a size-reducing apparatus.

Another type of granulation process wherein particle growth occurs uses a fluidized bed as the granulator. Such a process is described by Niks et al. in U.S. Pat. No. 4,219,589. In that process, a gas stream atomizes the liquid material to fine droplets which then solidify on nuclei in the fluidized bed. The solidified particles are then removed from the granulator and separated into three streams of particles on the basis of size. The stream of oversized particles are crushed, combined with the stream of undersized particles and returned to the fluidized bed.

Musters in European patent EP-A-0-141-436 describes a fluid bed granulation process in which the liquid material is discharged from a liquid distribution system in the form of a virtually closed, conical film. Nuclei from the bed are moistened with the liquid as they are carried through the conical film with the aid of a powerful gas stream.

Yet other granulation processes in which particle formation takes place are the pan and the drum granulation processes such as described in, for example, Nitrogen, No. 95, pgs. 31–36, May/June 1975.

Drawbacks of all of these methods are the significant amount of dust produced during the granulation process or generally present in the granulation unit and the resulting accumulation of the dust in the granulation unit. For the purposes of the present invention, "dust" is defined as particles with a diameter less than 0.7 millimeters. Generally, this dust is carried along by the air stream to the areas of the granulation unit, especially the top, not contacted frequently by granules and deposits there. As the deposits accumulate, large lumps break off and fall down to block the granulator and/or the liquid spray apparatus and thus seriously disturb the granulation process. As a general matter, when this occurs, the granulation process must be stopped and the granulator cleaned. The cleaning procedure and resulting production outage can last 8 to 24 hours depending on such factors as the degree of fouling, composition of the granules and the type of equipment.

The dust generated by and present in a granulation system is caused primarily by three sources. The major source is the granulator itself. For example, the granulator produces 3 tons of dust per hour in a urea plant with a plant capacity of 75 tons of urea per hour. A second source of dust originates from the stream of crushed oversized particles leaving the size-reducing apparatus. In state-of-the-art production techniques this stream is returned directly to the granulator. Between 10 and 20 wt. % of the crushed oversized particles have a diameter smaller than 1 mm, a large proportion of which is in the form of dust. In the aforementioned urea plant, for example, this crushed oversized particle stream returns between 0.6 and 1.7 tons of dust per hour to the granulator. A third source of dust is the stream of undersized particles. However, the amount of dust originating here is small in comparison with the two other sources and, for example, in the case of the aforementioned urea plant is less than 0.1 ton per hour. Only about 1 to 4 wt. % of this stream of smaller particles has a diameter smaller than 1 mm.

SUMMARY OF THE INVENTION

An object of the invention is to process granules produced by granulation in such a manner that the amount of product dust to which the granulator is exposed is greatly reduced. This dust reduction will result in a lower rate of dust deposition in the granulator, resulting in a lower cleaning frequency and, thus, higher production rates.

The present invention of a process for the production of granules from a liquid composition involves applying the liquid composition onto or over solid particles of the same composition recirculating in a granulation zone of a granulator, thereby causing solid particles of the composition to grow, and then withdrawing a stream of the grown solid particles from the granulation zone. This stream of grown solid particles is then cooled in a cooler. The cooled stream of grown solid particles is then separated by a size-sorting apparatus into streams based on the size of the grown solid particle; thus producing streams of undersized, oversized, and desiredsized grown solid particles. These three particle streams are each treated differently. The stream of undersized grown solid particles is returned to the granulation zone. The stream of oversized grown solid particles is transferred to a size-reducing apparatus to be crushed with the resulting stream of crushed solid particles being returned to the cooler. The stream of desired-sized grown solid particles is withdrawn and either stored for future sale or sent onto another process.

The applicant has found that the above object can be realized by supplying the crushed particle stream to a cooler downstream of the granulator, instead of to the granulator itself. This step reduces the amount of dust which accumulates in the granulator and thereby increases the time between production shutdowns due to granulator cleaning.

DETAILED DESCRIPTION OF THE INVENTION

Figure 1:
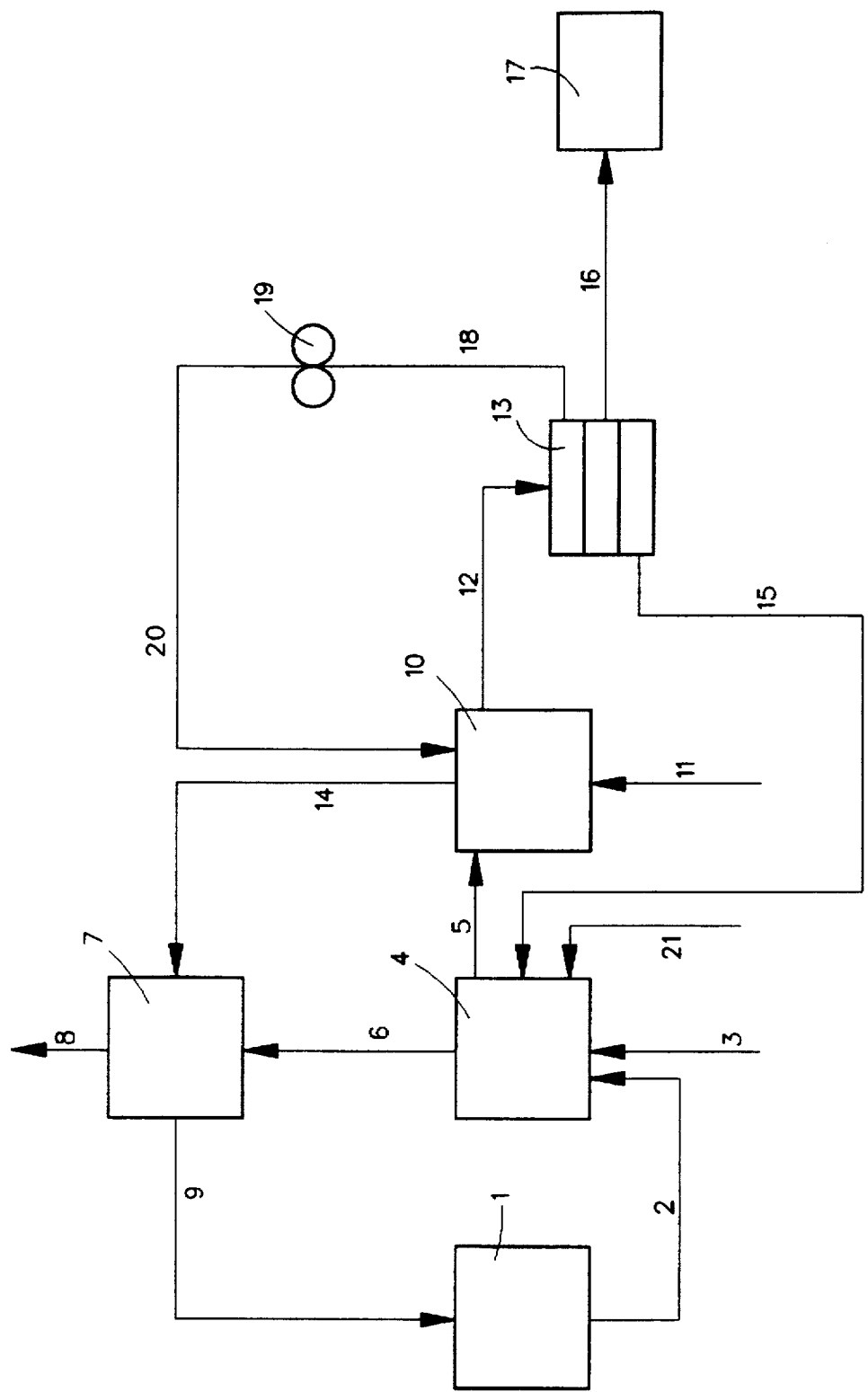
FIG. 1 is a schematic process diagram of an embodiment of the present invention.

The present process for the production of granules from a liquid composition, such as, for example, a solution, melt, or suspension, involves applying the liquid composition onto solid particles of the same composition recirculating in a granulation zone of a granulator, thereby causing solid particles of the composition to grow, and then discharging, when, for example, the solid particles grow to a selected size, a stream of the grown solid particles from the granulation zone. This stream of grown solid particles is then cooled in a cooler. The cooled stream of grown solid particles is then separated by a size-sorting apparatus, for example, a sizing sieve or screen, into streams based on the size of the grown solid particle; thus producing streams of undersized, oversized, and desired-sized grown solid particles. These particle streams are each treated differently. The stream of undersized grown solid particles is returned to the granulation zone. The stream of oversized grown solid particles is transferred to a size-reducing apparatus, for example, a double roll crusher, to be crushed with the resulting stream of crushed solid particles being recycled to the cooler. The stream of desired-sized grown solid particles is withdrawn from the process and either stored or sent onto another process.

Preferably, both the cooler and the granulator are operated at a slight underpressure. "Slight underpressure" means an underpressure of about 0 to 100 mm water, preferably 0 to 70 mm water.

This invention can be applied to all sorts of liquid compositions in the form of a solution, melt or suspension. Examples of suitable materials to be granulated are ammonium salts, such as ammonium nitrate, ammonium sulfate or ammonium phosphate as well as mixtures thereof, simple fertilizers such as calcium ammonium nitrate, magnesium ammonium nitrate, compound NP and NPK fertilizers, urea, urea-containing compositions, sulfur and the like. The invention is particularly suited for granulating simple and complex fertilizers and especially for granulating urea.

The invention can suitably be applied to various granulation processes in which both the undersized and the crushed oversized particles are recirculated entirely within the granulation process. Examples thereof are fluid bed granulation, spouted bed granulation, pan granulation or drum granulation processes, such as are described in Perry's Chemical Engineers' Handbook, pgs. 8–71, 20–59 to 20–74 (6th Ed., 1984), the complete disclosure of which is incorporated herein by reference.

The process according to the invention can be carried out in, for example, an installation, as generally described in, for example, U.S. Pat. No. 4,219,589, the complete disclosure of which is incorporated herein by reference, consisting of a granulator such as a fluid bed granulator, a cooler, a screening apparatus, an apparatus for crushing oversized particles and a gas/solid separating apparatus for separating solid particles from the gas stream leaving the granulator and/or the cooler.

FIG. 1 is a schematic representation showing one embodiment of the present invention. For the production of granules from a liquid composition, such as a urea solution, a solution of the liquid composition is passed from a storage vessel 1 via an evaporation step through line 2 to a granulator 4 and is sprayed into the granulator with or without the aid of a gas stream 3, whereby the granules form and are continuously discharged from the granulator via line 5.

The temperature in the storage vessel 1 is between, for example, about 50° C. and about 250° C., depending on the product to be granulated. In the case of urea granulation, the temperature in the storage vessel is between about 70° C. and about 100° C., in particular between about 75° C. and about 99° C. The temperature in the granulator is between about 60° C. and about 180° C. and in the case of urea granulation preferably between about 90° C. and about 140° C. The amount of gas in gas stream 3 is in the range from about 0 to about 0.9 kilogram per kilogram of liquid composition. The temperature of gas stream 3 is about 20° C. to about 180° C. and in the case of urea granulation preferably between about 90° C. and about 140° C.

In the case of a fluid bed or a spouted bed, fluidization gas, such as air, is supplied to the granulator through line 21. In the case of a pan or drum granulation process, ambient air is supplied to the granulator through line 21.

The gas stream leaving the granulator is passed through line 6 to a gas/solids separating apparatus 7 such as a cyclone or scrubber, where solid material, primarily dust, is separated from the gas carrying it, with the gas being discharged through line 8. The dust separated from the gas stream can be returned via line 9, optionally diluted with a solvent such as water, to the storage vessel 1 and resupplied to the granulator 4.

The granulate leaving the granulator 4 via line 5 is cooled in a cooler 10 with the aid of a gas stream 11 supplied to the cooler, whereafter the granulate is passed through line 12 to a size-sorting or screening apparatus 13. The temperature of the gas stream 11 supplied is about 10° C. about 80° C. and the amount is between about 0.5 and about 5 kilograms of gas per kilogram of granules supplied to the cooler. In the case of urea granulation the temperature of the gas stream is preferable between about 10° C. to about 50° C. and the temperature at which the urea granules exit the cooler is between about 20° C. and about 80° C., more preferably between about 25° C. and about 75° C.

The gas stream leaving the cooler 10 via line 14 is transferred to the aforementioned gas/solids separating apparatus 7. This separating apparatus 7 may be comprised of, for example, two separate apparatuses or a combined apparatus for cleaning the dust-laden air from the granulator 4 and/or the air from the cooler 10.

In the size-sorting or screening apparatus 13 the granulate is divided into three streams, namely oversized, desired-sized and undersized particles. The undersized particles are returned via line 15 to the granulator 4 to serve as nuclei on which solid particles of the liquid composition can grow during the granulation process. Desired-sized particles pass via provision 16 to storage 17 whereafter they may be sold or used in a downstream process. Oversized particles are passed through line 18 to a size-reducing or crusher apparatus 19 where they are converted into crushed particles with an average particle diameter of about 1.2 to about 2.4 mm, preferably about 1.5 to about 2.1 mm if the desired-sized product has a diameter of about 2 to about 4 mm. Dust formation is inherent in this crushing process. An overview of such crushing equipment can for example be found in Perry and Chilton Chemical Engineers Handbook, fifth edition pages 8–16 to 8–57. For the present invention especially the equipment called Roll-crushers as described in this reference on pages 8–19 to 8–22 are suitable.

In the case of urea granulation, the desired-sized particle usually has preferably a granule diameter of between about 2 and 4 mm. The oversized particle has a diameter greater than about 4 mm and the undersized particle has a diameter less than about 2 mm. However, other granule diameters are applicable also. In the case of, for example, the production of urea granules for forestry with aerial application, the granule diameter of a desired-sized particle is between 5 and 15 mm, preferably between 7 and 10 mm.

The crushed particles, along with the dust produced in the crushing process, are returned through line 20 to the cooler 10 downstream of the granulator 4. This step reduces the amount of dust which accumulates in the granulator and thereby increases the time between production shutdowns due to granulator cleaning.

This method for producing granules is described in patent application number 1002862 filed in The Netherlands on Apr. 15, 1996, the complete disclosure of which is hereby incorporated by reference.

The following non-limiting examples further describe the present invention.

EXAMPLES

Example 1

In a test set-up, urea was granulated in a fluid bed granulator at a temperature of about 110° C. in a cylindrical fluid bed having a diameter of 45 cm. The fluid bed was bounded on the underside by a porous plate 6% of which consisted of 1.8 mm diameter holes. Cold air flowed through the holes into the fluid bed at a superficial velocity of about 2 m/s. An overflow was provided at the top side of the bed 70 cm above the bottom plate. A liquid distributing device, as described in EP-A-0-141-436, was placed at the center of the bottom plate.

Urea melt at about 140° C. containing about 0.5 wt. % water was supplied at a rate of about 200 kg/h from a urea storage vessel to the fluid bed granulator while the liquid distributing device operated at about 140° C. with air supplied at a rate of about 90 kg/h. The urea granules emerging from the bed were cooled in a cooler to about 40° C. with the aid of a cold gas and then screened on flat-bed screens.

Approximately 200 kg/h of granules having a grain size between about 2 and 4 mm, 30 kg/h of granules greater than about 4 mm and 150 kg/h of granules less than about 2 mm were obtained. The small granules were returned directly to the fluid bed granulator. A stream of oversized granules of about 30 kg/h went to a size-reducing apparatus which consisted of a double roll crusher, adjusted for an average granule size of 1.4 mm. The crushed granules were supplied back to the cooler at a rate of about 30 kg/h.

Urea dust was extracted from the gas stream exiting the fluid bed granulator at a rate of about 8 kg/h and from the cooler at a rate of about 5 kg/h. These dust streams were passed to a gas/solid separator, where the urea dust was separated and added to the urea storage vessel.

After 29 days of continuous operation, the fluid bed granulator became blocked, and the test was terminated.

Comparative Example 1

Analogously to Example 1, urea was granulated in the test set-up of Example 1 except that the crushed particles were continuously returned directly to the fluid bed granulator. Urea dust was extracted from the gas stream exiting the fluid bed granulator at a rate of about 12 kg/h. The fluid bed granulator became blocked and the test was terminated after 12 days of continuous operation.

Example 2

Ammonium nitrate was granulated in a test set-up of a spouted bed granulator. The spouted bed was located in a cylindrical vessel of 45 cm diameter, which was provided at the underside with a conical section converging downward at an angle of 30 degrees to the vertical and terminating in the air supply pipe. Air at about 35° C. entered the apparatus at a rate of about 400 kg/h and a velocity of about 40 m/s. The granules in the spouted bed had a temperature of about 100° C. The overflow was located in the cylindrical section of the spouted bed, 30 cm above the transition from the conical section to the cylindrical section.

Ammonium nitrate melt at about 180° C., containing about 0.5 wt. % of water and about 1.5 wt. % of $Mg(NO_3)_2$, was spouted into the air stream at a rate of about 100 kg/h. The ammonium nitrate granules emerging from the spouted bed granulator were transferred to a cooler and cooled to about 40° C. and then screened on flat bed screens.

Approximately 100 kg/h of granules with a grain size between about 2 and 4 mm, 10 kg/h of granules greater than about 4 mm and 75 kg/h of granules less than about 2 mm were obtained. The granules less than about 2 mm were returned to the spouted bed granulator. The granules greater than about 4 mm were passed to a size-reducing apparatus, which was adjusted for an average grain size of 1.4 mm, and then returned to the cooler. Dust was extracted by a gas/solid separator from the gas streams exiting the spouted bed granulator at a rate of about 3 kg/h and at a rate of about 2 kg/h from the cooler.

The spouted bed granulator became blocked and the test was terminated after 27 day of continuous operation.

Comparative Example 2

As in Example 2, ammonium nitrate was granulated and particles with original diameters greater than about 4 mm were crushed in a size-reducing apparatus and supplied directly back to the spouted bed granulator. Dust was extracted by a gas/solid separator from the gas stream exiting the spouted bed granulator at a rate of about 5 kg/h. The spouted bed granulator became blocked and the test was stopped after 14 days of continuous operation.

What is claimed is:

1. A process for the production of granules from a liquid composition, said process comprising the steps of:

applying the liquid composition onto solid particles recirculating in a granulation zone of a granulator, thereby depositing and solidifying said liquid composition around said solid particles to increase the size of the particles and thereby form grown solid particles;

discharging a stream of said grown solid particles from the granulation zone to a cooler;

cooling said stream of said grown solid particles in said cooler to produce a cooled stream of said grown solid particles;

dividing, in a size-sorting apparatus, said cooled stream of said grown solid particles into individual streams based on the size of said grown solid particles to thereby produce streams of undersized, oversized, and desired-sized grown solid particles;

recycling said stream of said undersized grown solid particles to said granulation zone;

transferring said stream of said oversized grown solid particles to a size-reducing apparatus; crushing said stream of said oversized grown solid particles in said size-reducing apparatus, thereby reducing the particle size of said oversized grown solid particles and thereby producing a stream of crushed solid particles;

recycling said stream of said crushed solid particles to said cooler; and withdrawing said stream of desired-sized grown solid particles.

2. A process according to claim 1, wherein said granulator and said cooler are operated at an underpressure.

3. A process according to claim 2, wherein said underpressure in said granulator and said cooler is from about 0 to about 70 millimeters water.

4. A process according to claim 1, wherein said granulator is a fluid bed, spouted bed, pan or drum granulator.

5. A process according to claim 1, wherein said liquid composition is a simple or complex fertilizer.

6. A process according to claim 5, wherein said liquid composition is urea.

7. A process according to claim 1, wherein said stream of grown solid particles is cooled using a gas stream at a temperature of from about 10° C. to about 50° C. and said gas stream is supplied at a rate of from about 0.5 to about 5 kg of gas per kg of particles.

8. A process according to claim 1, wherein said desired-sized particles have an average particle diameter of about 2 to about 4 mm.

9. A process according to claim 8, wherein said crushed solid particles have an average particle diameter of about 1.2 to about 2.4 mm.

10. A process according to claim 9, wherein said crushed solid particles have an average particle diameter of about 1.5 to about 2.1 mm.

11. A process according to claim 1, wherein said liquid composition is a solution, melt, or suspension.

12. A process for the production of granules from liquid urea, said process comprising the steps of:

applying liquid urea onto solid urea particles recirculating in a granulation zone of a granulator, thereby depositing and solidifying liquid urea around said solid urea particles to increase the size of the particles and thereby form grown solid urea particles;

discharging a stream of said grown solid urea particles from the granulation zone to a cooler;

cooling said stream of said grown solid urea particles in said cooler to produce a cooled stream of said grown solid urea particles;

dividing, in a size-sorting apparatus, said cooled stream of said grown solid urea particles into individual streams based on the size of the grown solid urea particles to thereby produce streams of undersized, oversized, and desired-sized grown solid urea particles;

recycling said stream of said undersized grown solid urea particles to said granulation zone;

transferring said stream of said oversized grown solid urea particles to a size-reducing apparatus; crushing said stream of said oversized grown solid urea particles in said size-reducing apparatus, thereby reducing the particle size of said oversized grown solid urea particles and thereby producing a stream of crushed solid urea particles;

recycling said stream of crushed solid urea particles to said cooler; and withdrawing said stream of desired-sized grown solid urea particles.

13. In a process for producing urea granules by a granulation method in a granulator, wherein a stream of urea particles from a size-sorting apparatus is crushed in a size-reducing apparatus to produce a stream of crushed solid urea particles, wherein the improvement comprises the step of recycling said stream of crushed solid urea particles to a cooler located downstream of said granulator and upstream of said size-sorting apparatus.

* * * * *